(12) United States Patent
Allgeier et al.

(10) Patent No.: US 7,390,897 B2
(45) Date of Patent: Jun. 24, 2008

(54) METHOD FOR MAKING CAPROLACTAM FROM IMPURE 6-AMINOCAPRONITRILE

(75) Inventors: Alan M. Allgeier, Oak Park, CA (US); John J. Ostermaier, Orange, TX (US); Sourav K. Sengupta, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 313 days.

(21) Appl. No.: 11/083,715

(22) Filed: Feb. 10, 2006

(65) Prior Publication Data

US 2006/0211859 A1    Sep. 21, 2006
US 2008/0009618 A9    Jan. 10, 2008

(51) Int. Cl.
*C07D 201/08*    (2006.01)
(52) U.S. Cl. ...................................................... 540/539
(58) Field of Classification Search ................... 540/539
See application file for complete search history.

(56) References Cited

U.S. PATENT DOCUMENTS

| 2,301,964 | A | 11/1942 | Martin |
| 2,357,484 | A | 9/1944 | Martin |
| 6,716,977 | B1 | 4/2004 | Kirby et al. |

*Primary Examiner*—Bruck Kifle

(57) ABSTRACT

The invention relates to the field of production of lactams from aminonitriles, and in particular to the production of ε-caprolactam by the vapor phase hydrolytic cyclization of 6-aminocapronitrile. A crude liquid caprolactam comprising ε-caprolactam (CL), 6-aminocapronitrile (ACN) and water obtained from a vapor phase cyclization reaction of ACN is contacted with hydrogen in the presence of a hydrogenation catalyst to convert the ACN in the crude liquid caprolactam to a product comprising hexamethylenediamine (HMD) and hexamethyleneimine (HMI). Tetrahydroazepine (THA) in the crude liquid caprolactam is converted to HMI during this hydrogenation. The HMD and HMI have lower boiling points compared to ACN and thus they are more easily separated from CL in the subsequent distillation operations. Thus a process to make CL from ACN with fewer distillation stages, and with lower pressure drop and lower base temperature, is accomplished.

12 Claims, 2 Drawing Sheets

US 7,390,897 B2

METHOD FOR MAKING CAPROLACTAM FROM IMPURE 6-AMINOCAPRONITRILE

FIELD OF THE INVENTION

The present invention relates to the field of production of lactams from aminonitriles, and in particular to the production of ε-caprolactam by the vapor phase hydrolytic cyclization of 6-aminocapronitrile.

BACKGROUND OF THE INVENTION

ε-Caprolactam is a precursor for the preparation of Nylon-6. Nylon-6 was first made in 1899 by heating 6-aminohexanoic acid. Commercially feasible synthesis from ε-caprolactam (CL) was discovered by Paul Schlack at I. G. Farbenindustrie in 1938. Currently, approximately 95 wt % of the world's ε-caprolactam is produced from cyclohexanone oxime via the Beckmann rearrangement. The starting material for cyclohexanone can be cyclohexane, phenol, or benzene. Then, through a series of reductions and/or oxidations, cyclohexanone is formed. The latter is then reacted with a hydroxylamine salt, usually the sulfate, to form the oxime and ammonium sulfate. The oxime is rearranged in concentrated sulfuiric acid, and the resulting lactam sulfate salt is neutralized with ammonia to form ε-caprolactam and more ammonium sulfate. Subsequently, pure ε-caprolactam is obtained by a number of separation and purification steps. Currently, this process is extremely capital intensive and generates large quantities of waste.

An economically attractive method of production of ε-caprolactam uses 6-aminocapronitrile (ACN). U.S. Pat. No. 2,301,964 (E. I. Du Pont de Nemours & Company) discloses the production of lactams from aminonitriles and water in a liquid-phase method. Hydrolysis and concurrent lactam formation proceed rapidly when aminonitrile is reacted in a weak aqueous solution. Temperatures of from 200° C. to 375° C. are employed. The aminonitrile and water are maintained at this reaction temperature for not more than 1 hour. The reaction is preferably catalyzed with hydrogen sulfide.

U.S. Pat. No. 2,357,484 (issued to Martin, E. I. Du Pont de Nemours & Company) discloses a vapor-phase catalytic process for preparing N-substituted amides. The process comprises passing a vaporized mixture of water and an aliphatic aminonitrile, containing at least one aminonitrile moiety, over a dehydration-type catalyst at a temperature of typically from 150° C. to 500° C. for not more than 1 minute. When an open-chain aliphatic aminonitrile is used, in which the amino and nitrile groups are separated by at least two carbon atoms in contiguous relation, the product obtained is a lactam.

In recent years, inexpensive adiponitrile (ADN) has been made by the direct hydrocyanation of butadiene. This has led to a renewed interest in the Martin CL process because inexpensive ADN can be partially hydrogenated and refined to produce an impure product that comprises ACN. This product may contain some byproducts of the hydrogenation reaction, notably tetrahydroazepine (THA).

U.S. Pat. No. 6,716,977 discloses a method for making CL from impure ACN containing THA, comprising the following steps:

(1) Contacting the impure ACN with water at elevated temperature in the presence of a dehydration catalyst, both the impure ACN and the water being in the vapor phase, to produce a vapor phase reaction product that comprises CL, ammonia, water, ACN, and THA;

(2) Separating the ammonia and a major portion of the water from the vapor phase reaction product to produce a crude liquid CL comprising CL, ACN and THA;

(3) Introducing the crude liquid CL into a low boiler distillation column and removing a major portion of both the THA and ACN as a low boiler column distillate, and removing CL, high boilers and at most a minor portion of both the THA and ACN as a low boiler column tails; and (4) Introducing the low boiler column tails into a high boiler distillation column and removing CL and at most a minor portion of the high boilers as a high boiler column distillate product and removing a major portion of the high boilers as a high boiler column tails.

In this method, separation of ACN & THA from CL requires a considerable number of stages in the low boiler column due to the difficulty of separation. A large number of stages in this column will cause increased pressure drop and excessively high temperature in the base of the column. It would, therefore, be desirable to have a process to make CL from ACN in which the impurities in the crude caprolactam product were converted into species having a higher vapor pressure, which would require fewer distillation stages.

SUMMARY OF THE INVENTION

In the present invention, a crude liquid caprolactam comprising ε-caprolactam (CL), 6-aminocapronitrile (ACN) and water obtained from a vapor phase cyclization reaction of ACN is contacted with hydrogen in the presence of a hydrogenation catalyst to convert the ACN in the crude liquid caprolactam to a product comprising hexamethylenediamine (HMD) and hexamethyleneimine (HMI). Tetrahydroazepine (THA) is converted to HMI during this hydrogenation. The HMD and HMI have lower boiling points compared to ACN and thus are more easily separated from CL in the subsequent distillation operations. Thus a process to make CL from ACN with fewer distillation stages (hence lower pressure drop and lower base temperature) is accomplished. The present invention is, therefore, a method for making ε-caprolactam (CL) from 6-aminocapronitrile (ACN), comprising:

(a) contacting a vaporized mixture of ACN and water in a reactor comprising a dehydration catalyst to produce a vapor phase reaction product comprising CL, ammonia, water and ACN;

(b) separating the ammonia and a major portion of the water from the vapor phase reaction product to produce a crude liquid caprolactam comprising CL, ACN and a minor portion of the water;

(c) contacting the crude liquid caprolactam with hydrogen in the presence of a hydrogenation catalyst to produce a hydrogenated crude caprolactam comprising CL, HMI, HMD and water;

(d) removing water and HMI from the hydrogenated crude caprolactam in a dehydration column to produce an anhydrous crude caprolactam comprising CL and HMD;

(e) introducing the anhydrous crude caprolactam into a low boiler distillation column, wherein the low boiler column distillate comprises HMD, and the low boiler column tails comprises CL and high boilers; and (f) introducing the low boiler column tails into a high boiler distillation column, wherein and the high boiler column distillate comprises CL and the high boiler column tails comprises high boilers.

BRIEF DESCRIPTION OF THE DRAWING

The Drawing consists of two figures, FIGS. 1 and 2, which are flow diagrams illustrating two alternative embodiments of the process of the present invention.

DETAILED DESCRIPTION OF THE INVENTION

Figure 1:
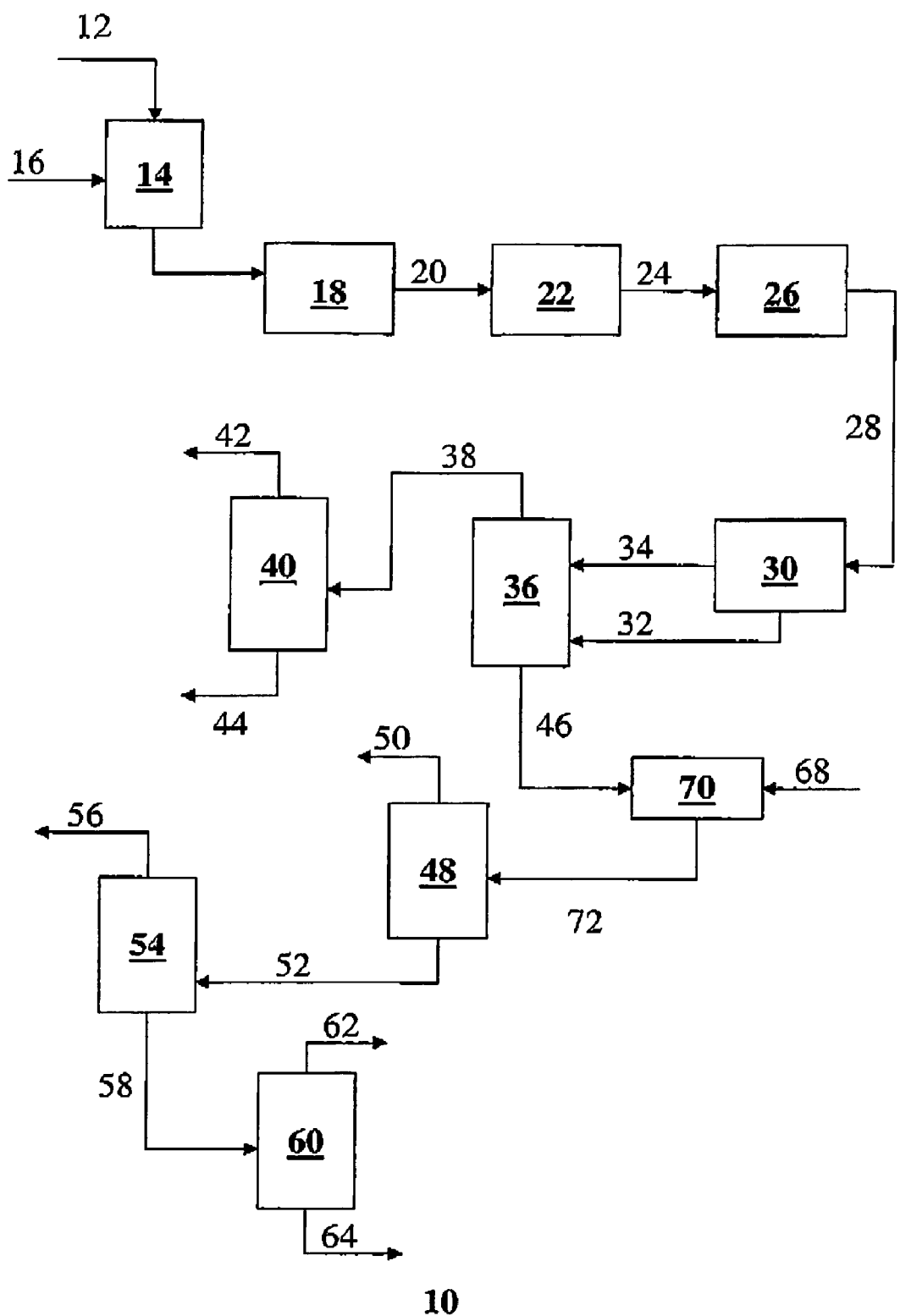
Figure 2:
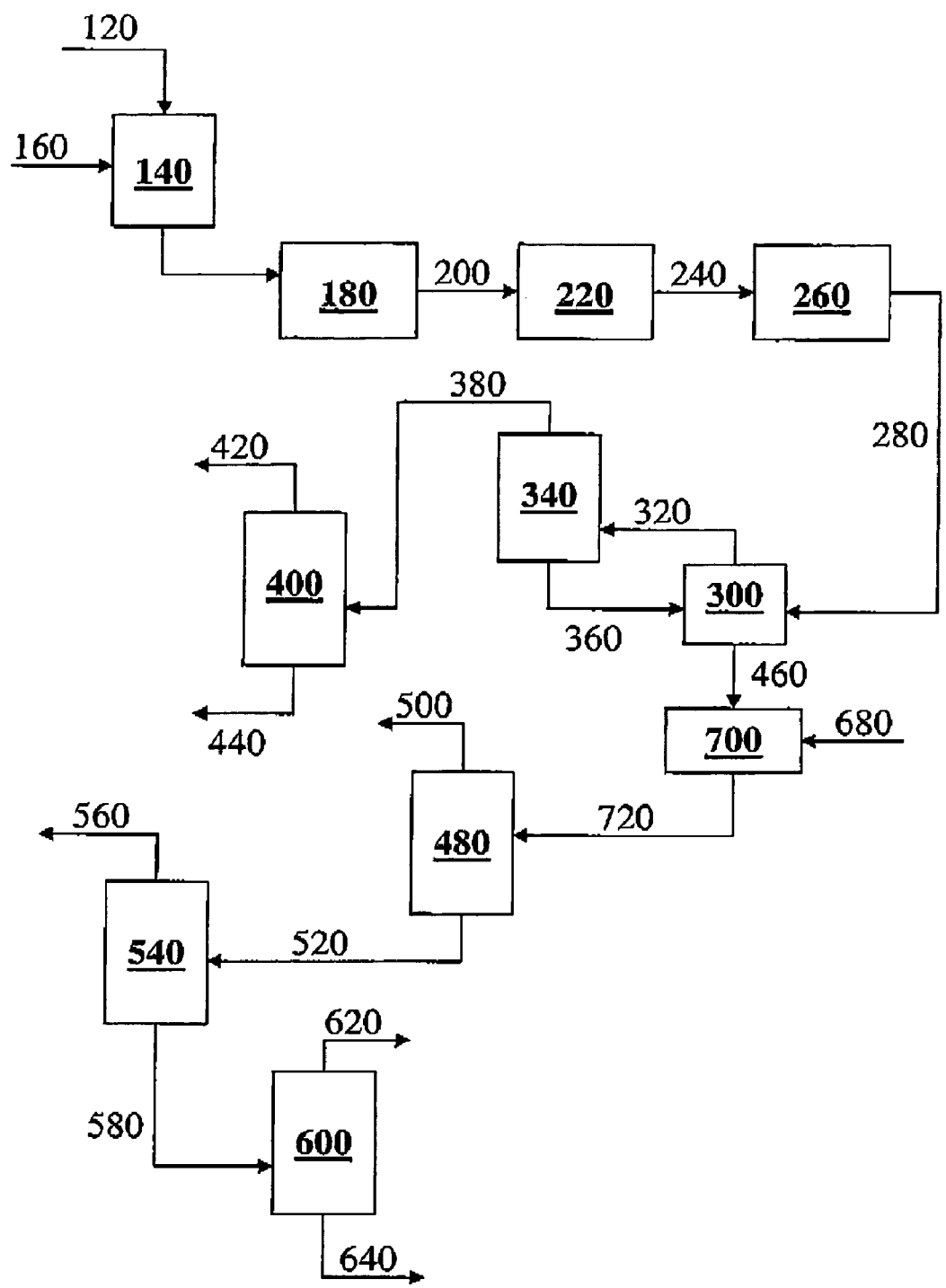

A systematic description of one embodiment of the invention follows. A stream of 6-aminocapronitrile (ACN), that optionally comprises tetrahydroazepine (THA) and dimer of ACN, and a stream of water are introduced into a mixer. The molar ratio of water to ACN is maintained in the range of about 1:1 to 10:1. The ACN stream can contain about 0 to about 1200 ppm tetrahydroazepine (THA) and about 0 to about 2 wt % dimer of ACN. The ACN stream and water stream should contain less than about 0.1 wt % dissolved oxygen, which can be accomplished by blanketing the ACN and water with nitrogen prior to feeding to the mixer. The mixer intimately mixes the ACN stream and water stream. A static mixer, such as a Kenix® mixer, can be used. A liquid mixture of ACN and water produced by the mixer is introduced into a vaporizer in which heat is supplied to vaporize the liquid mixture to produce a vapor mixture of ACN and steam. Electrical heating, process to process heat transfer, steam or a hot oil system, using a suitable heat transfer fluid, such as a material sold by Dow Chemical Company under the trademark "Dowtherm-A," can be used to supply heat. The vapor mixture is preferably at a temperature in the range of about 160° C. to about 190° C. and a pressure below about 30 psig (323 kPa). The vapor mixture is introduced into a superheater in which the vapor mixture is further heated to a temperature in the range of about 220° C. to about 300° C. to produce a superheated mixture of ACN vapor and steam. Electrical heating, process to process heat transfer, high-pressure steam or a hot oil system, using a suitable heat transfer fluid, such as a material sold by Dow Chemical Company under the trademark "Dowtherm-A," can be used to supply heat to the superheater.

The superheated vapor exits the superheater and is fed into a caprolactam synthesis reactor. The reactor contains a dehydrating catalyst, as taught by Martin, such as activated alumina, titanium dioxide, vanadium oxide, etc. The reactor can be a fixed bed or a fluidized bed reactor.

The heat of reaction is removed from the reactor by a heat transfer fluid (not shown) that preferably controls the reaction temperature within a range of about 250° C. to about 325° C. A suitable heat transfer fluid is the material sold by Dow Chemical Company under the trademark "Dowtherm-A." Alternatively, the reactor may comprise a plurality of adiabatic packed bed reaction zones arranged in succession with inter-stage cooling. The reaction occurring inside the reactor produces CL and ammonia.

Exiting the reactor is a vapor phase product stream that comprises about 30 wt % to about 70 wt % CL, a corresponding stoichiometric amount of ammonia, about 30 wt % to about 70 wt % water, about 0 to about 5 wt % unreacted ACN, and about 0 to about 1 wt % THA. The product stream is fed into a partial condenser, operating at a temperature preferably greater than about 150° C. and a pressure in the range of about 1 atm to about 2 atm (101 to 203 kPa). The partial condenser condenses some of the water, the CL, the unreacted ACN and substantially all of the THA that might be present to produce a liquid stream. The liquid stream comprises greater than about 90 wt % and preferably greater than about 99 wt % CL, less than about 5 wt % and preferably less than about 1 wt % ACN, about 0 to about 5 wt % water, about 900 ppm THA, about 300 ppm hexamethyleneimine (HMI), and less than about 1000 ppm dimer of ACN. Also exiting the condenser is a vapor stream that comprises water vapor and ammonia gas (about 10 wt % to about 20 wt % $NH_3$ and about 80 wt % to about 90 wt % water).

Both the liquid stream and the vapor stream are fed into different stages of an ammonia removal distillation column. The liquid stream is fed to the lower part of the column, while the vapor stream is fed into a stage above the one into which the liquid stream is fed. The ammonia removal distillation column contains trays and operates at a pressure slightly above atmospheric pressure (e.g. about 1 atm to about 2 atm, i.e. about 101 kPa to about 203 kPa), at a temperature in the range of about 100° C. to about 160° C. and with a reflux ratio in the range of about 0.1 to 0.5. The ammonia removal distillation column removes substantially all of the ammonia as a distillate along with most of the water. The distillate composition is about 10 wt % to about 20 wt % $NH_3$, about 0 to about 0.5 wt % HMI, and about 80 wt % to about 90 wt % water.

The distillate is fed into a high pressure ammonia refining column that contains trays, and that operates with a reflux ratio of about 0.1 to 1. From the ammonia refining column anhydrous ammonia product is removed as a distillate and water (together with less than about 0.5 wt % organic materials) is removed as a column tails. The pressure in the ammonia refining column can vary, depending upon the temperature of available heat removal fluids.

The ammonia removal distillation column produces a crude liquid caprolactam as a column tails that comprises less than about 5 wt % water, about 0 to about 10 wt % unreacted ACN, less than about 0.5 wt % unreacted THA, greater than about 90 wt % CL, and some high boilers. The ammonia removal column can contain trays or packing, and is preferably operated with a tails temperature below about 160° C. to minimize the formation of CL oligomers.

The ammonia removal distillation column tails comprising crude liquid caprolactam is contacted with a stream of hydrogen in a hydrogenation reactor to produce a hydrogenated crude caprolactam. ACN and THA in the crude caprolactam react with hydrogen to produce HMD and HMI. The molar ratio of hydrogen to CL in the crude liquid caprolactam column tails is in the range of about 1:50 to 1:1. The hydrogenated crude caprolactam contains about 0.2 wt % HMI, about 0 to about 5 wt % HMD, less than about 50 ppm THA, and less than about 300 ppm ACN. The hydrogenation reactor is maintained at about 50° C. to about 130° C. and about 50 psia to about 2,500 psia (about 345 kPa to about 17,237 kPa) pressure, preferably about 200 psia to about 600 psia (about 1,379 kPa to about 4,137 kPa).

The hydrogenation reactor contains a hydrogenation catalyst (not shown). The hydrogenation catalyst can be based on elements of the transition metal groups of the periodic table, such as Ni, Co, Rh, Pd, and Pt. Promoter elements may be added to the catalyst to improve the activity and selectivity of the catalyst. Examples of suitable promoters are lithium, sodium, potassium, magnesium, calcium, titanium, molybdenum, chromium, iron, palladium, platinum, copper, aluminum, and silicon. There are a variety of ways known in the art for preparing the catalysts, and many catalysts are commercially available. The catalysts may comprise a support material such as carbon, alumina, or silica, or they could be provided without a support material, for example in the form of sponge metal catalysts, known as Raney-type catalysts, or reduced metal oxides, which are nominally all metallic in content. A preferred catalyst is Raney® Ni.

The hydrogenated crude caprolactam is fed into a vacuum dehydration column, operating at a temperature in the range of about 60° C. to about 150° C., a pressure in the range of about 20 mm Hg to about 100 mm Hg (about 2.7 kPa to about 13.3 kPa), and a reflux ratio of approximately 0.5. The vacuum dehydration column contains structured packing. Water and HMI are removed from the dehydration column as a dehydration column distillate that contains about 30 wt % to about 70 wt % HMI and about 30 wt % to about 70 wt % water. A dehydration column tails is removed from the dehydration column. The dehydration column tails comprises about 95 wt % to about 99.5 wt % CL, about 0.1 wt % to about 5 wt % HMD, and less than about 1 wt % high boilers. Preferably, the dehydration column is operated with a tails temperature below about 160° C. to minimize the formation of CL oligomers, which are either a yield loss or can otherwise complicate the process.

The dehydration column tails is fed into a vacuum low boiler distillation column, operating with a tails temperature below about 160° C. The low boiler column contains structured packing and is operated at a pressure in the range of about 5 mm Hg absolute to about 40 mm Hg absolute (about 0.7 kPa to about 5.3 kPa), and preferably at about 10 mm Hg absolute (about 1.3 kPa) with a reflux ratio in the range of about 20 to 50. A low boiler column distillate is removed from the low boiler column. The low boiler column distillate comprises unreacted HMD and some CL, e.g. about 50 wt % HMD and about 50 wt % CL. A low boiler column tails is removed from the low boiler column 54. The low boiler column tails comprises CL and less than about 1 wt % high boilers.

The low boiler column tails is fed into a high boiler distillation column that contains structured packing. The high boiler distillation column operates at a sub-atmospheric pressure, e.g. in the range of about 10 mm Hg absolute to about 40 mm Hg absolute (about 1.3 kPa-about 5.3 kPa), and preferably about 10 mm Hg absolute (about 1.3 kPa) and with a tails temperature below about 160° C. The reflux ratio is less than about 1. High boilers and a minor portion (less than about 5 wt %) of the incoming CL are removed as a high boiler column tails. The majority (greater than about 95 wt %) of the incoming CL is removed as a high boiler column distillate. This high boiler column distillate has greater than 99.5% purity of CL. If desired, the high boiler column tails can be fed to a wiped film evaporator (not shown) to recover CL that is present in the high boiler column tails. This recovered CL can be fed to the high boiler distillation column.

If the present process is operated on a commercial scale, a substantial amount of water will result in the high pressure ammonia refining column tails and the dehydration column distillate streams. To increase the economic efficiency of the process, these streams may be combined, appropriately treated, and recycled back to the process.

A systematic description of a second embodiment of the invention follows. A stream of 6-aminocapronitrile (ACN), optionally comprising THA and dimer of ACN, and a stream of water are introduced into a mixer. The molar ratio of water to ACN is maintained in the range of about 1:1 to 10:1. The ACN stream can contain about 0 to 1200 ppm tetrahydroazepine and about 0 to 2 wt % dimer of ACN. The ACN stream and the water stream should contain less than about 0.1 wt % dissolved oxygen, which can be accomplished by blanketing the ACN and water with nitrogen before feeding to the mixer. The mixer intimately mixes the ACN stream and water stream. A static mixer, such as a Kenix® mixer can be used. A liquid mixture of ACN and water produced by the mixer is introduced into a vaporizer in which heat is supplied to produce a vapor mixture of ACN and steam. Electrical heating, process to process heat transfer, steam or a hot oil system, using a suitable heat transfer fluid, such as a material sold by Dow Chemical Company under the trademark "Dowtherm-A," can be used to supply heat. The vapor mixture is at a temperature in the range of about 160° C. to about 190° C. and a pressure less than about 30 psig (about 323 kPa). The vapor mixture is introduced into a superheater in which the vapor mixture is further heated to a temperature in the range of about 220° C. to about 300° C. to produce a superheated mixture of ACN vapor and steam. Electrical heating, process to process heat transfer, high-pressure steam or a hot oil system, using a suitable heat transfer fluid, such as a material sold by Dow Chemical Company under the trademark "Dowtherm-A," can be used to supply heat to the superheater.

The superheated vapor exits the superheater and is fed into a CL synthesis reactor. The reactor contains a dehydrating catalyst, as taught by Martin, such as activated alumina, titanium dioxide, vanadium oxide, etc. The reactor can be a fixed bed or a fluidized bed reactor.

The heat of reaction is removed from the reactor by a heat transfer fluid that preferably controls the reaction temperature within a range of about 250° C. to about 325° C. A suitable heat transfer fluid is the material sold by Dow Chemical Company under the trademark "Dowtherm-A." Alternatively, the reactor may comprise a plurality of adiabatic packed bed reaction zones arranged in succession with inter-stage cooling. The reaction occurring inside the reactor produces CL and ammonia.

Exiting the reactor is a vapor phase product stream that comprises about 30 wt % to about 70 wt % CL, a corresponding stoichiometric amount of ammonia, about 30 wt % to about 70 wt % water, about 0 to about 5 wt % unreacted ACN and about 0 to about 1 wt % THA. In this embodiment, the vapor phase product stream is fed directly, without condensing, to the lower part of an ammonia removal distillation column. The ammonia removal column contains trays and operates at a pressure slightly above atmospheric pressure (e.g. about 1 atm to about 2 atm, i.e., about 101 kPa to about 203 kPa) at a tails temperature in the range of about 100° C. to about 170° C. and with a reflux ratio in the range of about 0.1 to 5. The ammonia removal column removes substantially all of the ammonia and most of the water in an overhead stream. The ammonia removal column is equipped with a condenser having sufficient capacity to condense the overhead stream to produce a liquid reflux stream, a liquid distillate stream and a minor non-condensable vapor vent stream.

Alternatively, the vapor phase product stream can be passed through a cooler to cool the vapor, but not to a temperature below its dew point, as a means of reducing the requirements on condenser while still limiting the formation of CL oligomers. The cooling medium for the cooler can be, but is not limited to, circulating cooling water, air, other process streams, or other heat-exchange fluids.

The liquid distillate is fed into a high-pressure ammonia refining column containing trays and operating with a reflux ratio in the range of about 0.1 to 1, from which anhydrous ammonia product is removed as a distillate, and water (together with less than about 0.5 wt % of organic materials) is removed as a column tails. The pressure in the ammonia refining column can vary, depending upon the temperature of available heat removal fluids.

The ammonia removal column produces a crude liquid caprolactam as a column tails that comprises less than about 0.5 wt % water, about 0 to about 10 wt % unreacted ACN, less than about 0.5 wt % THA, greater than about 90 wt % CL, and less than about 3 wt % high boilers. The ammonia removal column can contain trays or packing, and preferably is operated with a tails temperature below about 160° C. to minimize the formation of CL oligomers.

The crude liquid caprolactam is contacted with a stream of hydrogen in a hydrogenation reactor to produce a hydrogenated crude caprolactam. ACN and THA in the crude caprolactam react with hydrogen to produce HMD and. HMI. The molar ratio of hydrogen to CL in the crude liquid caprolactam is in the range of about 1:50 to 1:1. The hydrogenated crude caprolactam contains about 0.2 wt % HMI, about 0 to about 5 wt % HMD, less than about 50 ppm THA, and less than about 300 ppm ACN. The hydrogenation reactor is maintained at about 50° C. to about 130° C. and about 50 psia to about 2,500 psia (about 345 kPa to about 17,237 kPa) pressure, preferably about 200 psia to about 600 psia (about 1,379 kPa to about 4,137 kPa).

The hydrogenation reactor contains a hydrogenation catalyst. The hydrogenation catalyst can be based on elements of the transition metal groups of the periodic table, such as Ni, Co, Rh, Pd, and Pt. Promoter elements may be added to the catalyst to improve the activity and selectivity of the catalyst. Examples of suitable promoters are lithium, sodium, potassium, magnesium, calcium, titanium, molybdenum, chromium, iron, palladium, platinum, copper, aluminum, and silicon. There are a variety of ways known in the art for preparing the catalysts, and many catalysts are commercially available. The catalysts may comprise a support material such as carbon, alumina, or silica, or they could be provided without a support material, for example in the form of sponge metal catalysts, known as Raney-type catalysts, or reduced metal oxides, which are nominally all metallic in content. The preferred catalyst is Raney® Ni.

The hydrogenated crude caprolactam is fed into a vacuum dehydration column operating at a temperature in the range of about 60° C. to about 150° C., a pressure in the range of about 20 mm Hg absolute to about 100 mm Hg absolute (about 2.7 kPa to about 13.3 kPa), with a reflux ratio of approximately 0.5. The vacuum dehydration column contains structured packing. Water and HMI are removed from the dehydration column as a dehydration column distillate containing about 30 wt % to about 70 wt % HMI and about 30 wt % to about 70 wt % water. A dehydration column tails is removed from the dehydration column. The dehydration column tails comprises about 95 wt % to about 99.5 wt % CL, about 0.1 wt % to about 5 wt % HMD, and less than about 1 wt % high boilers. Preferably, the vacuum dehydration column is operated with a tails temperature below about 160 ° C. to minimize the formation of CL oligomers, which are a yield loss or can otherwise complicate the process.

The dehydration column tails is fed into a low boiler distillation column, which operates with a tails temperature below about 160 ° C. and at a sub-atmospheric pressure. The low boiler column contains structured packing (not shown) and it operates at a pressure in the range of about 5 mm Hg absolute to 40 mm Hg absolute (about 0.7 kPa to 5.3 kPa), and preferably at about 10 mm Hg absolute (about 1.3 kPa), with a reflux ratio in the range of about 20 to 50. A low boiler column distillate is removed from the low boiler column. The low boiler column distillate comprises HMD and CL (approximately 50 wt % HMD, 50 wt % CL). A low boiler column tails is removed from the low boiler column. The low boiler column tails comprises CL and less than about 1 wt % high boilers.

The low boiler column tails is fed into a high boiler distillation column, containing structured packing and operating at a sub-atmospheric pressure (e.g., in the range of about 10 mm Hg to about 40 mm Hg absolute, i.e., about 1.3 kPa to about 5.3 kPa, and preferably at about 10 mm Hg absolute, i.e., about 1.3 kPa), with a tails temperature below about 160° C., and with a reflux ratio less than about 1. High boilers and a minor portion (less than about 5 wt %) of the incoming CL are removed as high boiler column tails. The majority (greater than about 95%) of the incoming CL is removed as a high boiler column distillate. This CL in the high boiler column distillate has greater than about 99.5% purity. If desired, the high boiler column tails can be fed to a wiped film evaporator (not shown) to recover CL that is present in the high boiler column tails. This recovered CL can be fed to the high boiler distillation column.

If the present process is operated on a commercial scale, a substantial amount of water will result in the high pressure ammonia refining column tails and the dehydration column distillate streams. To increase the economic efficiency of the process, these streams may be combined, appropriately treated, and recycled back to the process.

EXAMPLES

Example 1

Caprolactam Production Apparatus

A two-stage adiabatic reactor was used to demonstrate the vapor phase synthesis of ε-caprolactam (CL) by the hydrolytic cyclization of 6-aminocapronitrile (ACN). The experimental setup comprised of:

Two feed drums, one containing distilled water, and the other ACN. Both feed drums were kept under a blanket of nitrogen and were previously sparged with nitrogen to remove dissolved oxygen.

A vaporizer consisting of a jacketed 1½ inch stainless steel pipe and heated with 140 psig (965 kPa) steam in the jacket. The vaporizer was fed from the feed drums by two metering pumps. A static mixer was attached between the vaporizer and pumps to ensure complete mixing of the reactants. A line was attached to the bottom of the vaporizer to take a blow-down purge from the vaporizer, if needed.

An electrically-heated superheater, which took the vapor from the vaporizer and superheated it to the desired inlet temperature of the reactor.

An adiabatic reactor with two stages—Stage 1 and Stage 2.

The Stage 1 reactor was well-insulated and made from a 3 ft. length of 1½ inch dia. stainless steel pipe. This reactor was charged with catalyst pellets and contained four electrical heaters. Two of the heaters, wrapped around the reactor were manually controlled by powerstats designed to supply the heat lost through the insulation of the reactor, which can be substantial at this very small experimental scale where surface area to volume ratios are significantly larger than at commercial manufacturing scale. Two other heaters were added, one at each end of the reactor to take care of heat losses at the ends. These were automatically controlled to set temperatures, measured by thermocouples placed between the heaters and the ends of the reactor. A thermowell was installed down the length of the reactor, which contained two multi-point thermocouples to measure nineteen temperatures down the reactor length.

The Stage 2 reactor was well-insulated and made from a 7 ft long and 1½ inch dia. stainless steel pipe. This reactor was charged with catalyst pellets and contained four electrical heaters as was done on the Stage 1 reactor. This reactor contained one internal thermocouple at each end of the reactor to monitor the inlet and exit temperatures.

A heated transfer line, which acted as a cooler, connected the two stages of the reactor.

The condenser system was a two stage apparatus. Stage one effected the majority of the condensation and stage two provided final condensation of condensable materials mixed with the evaporating ammonia.

A product receiver (55 gallon drum) to collect the crude caprolactam solution for further work-up and analysis.

Caprolactam Production

An aqueous caprolactam (CL) solution was prepared by the hydrolytic cyclization of 6-aminocapronitrile (ACN) in the vapor phase using activated alumina catalyst, as described by E. L. Martin in U.S. Pat. No. 2,357,484. The first and second stages of the reactor were filled respectively with 600 g and 1197 g of 1/8" cylindrical extrudates of activated alumina catalyst. 20 g/min of ACN and 40 g/min of water were mixed together in the mixer, and vaporized in the vaporizer at 186° C., using 140 psig (965 kPa) steam on the shell-side of the vaporizer. The vapor stream exiting from the vaporizer was then superheated to 220° C. and the reactants, containing 33 wt % ACN in superheated steam, were fed to the 2-stage reactor system at a weight hourly space velocity of 0.7 $h^{-1}$. The first and second stages of the reactor ran with inlet/exit temperatures of approximately 256° C./312° C., and 260° C./312° C., respectively, for a total time on stream of 5 hours. A transfer line conveyed material between the reactor stages and also served to dissipate heat. The composition of the product stream as a function of time on stream is presented in Table 1. Data are given as weight percent composition on an organics-only basis. The product stream comprised about 70 wt % water.

TABLE 1

| Time on Stream (h) | ACN (wt %) | CPL (wt %) |
|---|---|---|
| 0 | 1.3 | 97.8 |
| 4 | 1.6 | 98.1 |
| 5 | 1.5 | 98.2 |

The composite product (i.e. product collected and combined over the entire course of the above reaction) comprised aqueous caprolactam and 1.35 wt % ACN on an organics-only basis. This product was divided in half for use in the comparative example and inventive example.

Comparative Example

Distillation

The above caprolactam solution comprised 1.35 wt % ACN (on an organics-only basis) and non-detectable levels of hexamethyleneimine (HMI). This material was distilled in a batch still with 2 inch diameter and containing 4.5 feet of wire mesh packing (Koch BX). The reboiler was a 2 liter round bottom flask.

The water was first removed at a column head pressure of 200 torr (27 kPa) using a reflux ratio of less than 1. During this step the reboiler was continuously fed aqueous CL solution and water was withdrawn as distillate. During this step the reboiler temperature increased as the concentration of CL in the reboiler increased. When the reboiler temperature reached 140° C. and the reboiler was full, the feed was stopped.

At this point the column head pressure was reduced to 10 torr (1.3 kPa), and the reflux ratio was increased to 50. During this stage of the distillation the impurities having a higher volatility than CL were removed. The principal impurity removed during this step is ACN. A series of five consecutive distillate cuts of 50 ml volume each were taken. Analysis of these cuts by gas chromatography gave the results in Table 2.

TABLE 2

| Cut # | ACN (wt %) |
|---|---|
| 1 | 12.7 |
| 2 | 1.7 |
| 3 | 0.4 |
| 4 | 0.2 |
| 5 | 0.1 |

At this point the reflux ratio was reduced to 2, and a 90 ml strip-cut was taken to flush the column. This was followed by a succession of 185 ml product cuts. The first of these product-cuts contained 0.03 wt % ACN. After removing the purified CL overhead a heel remained in the pot, which comprised 1.7 wt % high boiling impurities.

Inventive Example

Hydrogenation and Distillation

The product solution from the caprolactam production was charged to a distillation apparatus to remove a cut comprising ammonia and water and to yield a tails product comprising approximately 70 wt % caprolactam(aq) and 0.9 wt % 6-aminocapronitrile (i.e. 1.3 wt % on an organics-only basis). A portion (1960 g) was charged to an approx. 4-liter autoclave with 40 g of Raney® Ni 2800 slurry catalyst and about 40 g water. The reactor was purged with hydrogen and tested for leaks. The charge was heated to nearly 90° C. while stirring and then the pressure was increased to 900 psig (6205 kPa). The reaction mixture was maintained at 90° C. and 900 psig (6205 kPa) for five hours at which point the reactor was cooled and the mixture discharged. Reaction times less than five hours are also effective in the process of this invention. The product comprised 0.42 wt % hexamethyleneimine (HMI), 0.47 wt % hexamethylenediamine (HMD), no detectable ACN and approximately 0.4 wt % high boilers (on an organics-only basis).

The same distillation apparatus of the Comparative Example was used in the following steps. The water removal step was performed using the same procedure as used in the Comparative Example. During this step substantially all of the HMI was removed with the water, as water and HMI form a low boiling azeotrope.

The removal of impurities having a higher volatility than CL was performed at 10 torr head pressure and a reflux ratio of 20. The principal impurity removed during this step was HMD. In this Example, a lower reflux ratio was used because HMD is known to be more volatile than ACN. A series of two distillation cuts of 50 ml volume each were taken. Analysis of these cuts by gas chromatography gave the results presented in Table 3.

TABLE 3

| Cut # | HMD (wt %) |
|---|---|
| 1 | 5.8 |
| 2 | 0.4 |

At this point the reflux ratio was reduced to 2, and a 80 ml strip-cut was taken to flush the column. This was followed by succession of 185 ml product cuts. The first of these product cuts contained 0.03 wt % HMD. After removing the major portion of the purified CL overhead, a heel remained which comprised 1 wt % high boiling impurities.

In the Comparative Example it was necessary to operate at a reflux ratio of 50 and take five low boiler cuts of 50 ml each in order to reduce the ACN level of the first product cut to 0.03 wt %. In the Inventive Example the HMD content of the first product cut was reduced to 0.03 wt % by using a reflux ratio of 20 and by taking only two low boiler cuts. These examples illustrate that removal of impurities is greatly facilitated by hydrogenating the aqueous CL solution prior to distillation.

Example 2

This example is intended to show that hydrogenation of CL prior to distillation to convert ACN to HMD reduces the number of theoretical stages required to remove volatile impurities when the distillation is performed continuously. These examples were generated by calculation using conventional techniques known to persons skilled in the art of distillation.

Anhydrous CL containing 0.5 wt % ACN is fed to a distillation column operating with a reflux ratio of 40, and a head pressure of 10 torr (1.3 kPa). The design objective is to obtain a distillate product containing 40 wt % ACN and a tails stream containing 0.0001 wt % ACN. In order to achieve this objective a total of 18 theoretical stages are required, which gives a reboiler temperature of 162° C., assuming a pressure drop of 1 torr (0.13 kPa) per stage.

Anhydrous CL containing 0.5 wt % HMD is fed to a distillation column operating with a reflux ratio of 40, and a head pressure of 10 torr (1.3 kPa). The design objective is to obtain a distillate product containing 40 wt % HMD and a tails stream containing 0.0001 wt % HMD. In order to achieve this objective a total of 7 theoretical stages are required, which gives a reboiler temperature of 148° C., assuming a pressure drop of 1 torr (0.13 kPa) per stage.

Converting the ACN to HMD by hydrogenation allows the number of theoretical stages to be reduced from 18 to 7, which reduces the cost of the column. It also allows the reboiler temperature to be reduced from 162° C. to 148° C., which in turn reduces the amount of thermal degradation of CL that occurs during refining.

What is claimed is:

1. A method for making $\epsilon$-caprolactam (CL) from 6-aminocapronitrile (ACN), comprising:
   (a) contacting a vaporized mixture of ACN and water in a reactor, the reactor comprising a dehydration catalyst, to produce a vapor phase reaction product comprising CL, ammonia, water and ACN;
   (b) separating the ammonia and a major portion of the water from the vapor phase reaction product to produce a crude liquid caprolactam comprising CL, ACN and a minor portion of the water;
   (c) contacting the crude liquid caprolactam with hydrogen in the presence of a hydrogenation catalyst in a hydrogenation reactor to produce a hydrogenated crude caprolactam comprising CL, hexamethyleneimine (HMI), hexamethylenediamine (HMD) and water;
   (d) removing water and HMI from the hydrogenated crude caprolactam in a dehydration column to produce an anhydrous crude caprolactam comprising CL and HMD;
   (e) introducing the anhydrous crude caprolactam into a low boiler distillation column, wherein the low boiler column distillate comprises HMD, and the low boiler column tails comprises CL and high boilers; and
   (f) introducing the low boiler column tails into a high boiler distillation column, wherein the high boiler column distillate comprises CL and the high boiler column tails comprises high boilers.

2. The method of claim 1 wherein step (b) comprises:
   (a) partially condensing the vapor phase reaction product to produce a vapor stream comprising ammonia and water, and a liquid stream comprising water, caprolactam, and unreacted ACN;
   (b) introducing the vapor stream into a predetermined stage of a distillation column and introducing the liquid stream into a stage of the distillation column lower than the predetermined stage; and then
   (c) withdrawing a crude liquid caprolactam comprising caprolactam and a minor portion of the water from the bottom of the distillation column.

3. The method of any one of claims 1 and 2 wherein the crude liquid caprolactam comprises about 0 to about 50 wt % water.

4. The method of claim 3 wherein the crude liquid caprolactam comprises about 20 wt % water.

5. The method of claim 3 wherein the hydrogenation catalyst comprises one or more metals of the transition metal group.

6. The method of claim 3 wherein the hydrogenation catalyst comprises Raney Ni.

7. The method of claim 3 wherein the temperature in the hydrogenation reactor is in the range of about 80° C. to 130° C.

8. The method of claim 3 wherein the pressure in the hydrogenation reactor is in the range of about 50 psia to 2,500 psia (about 345 kPa to about 17,237 kPa).

9. The method of claim 3 wherein the pressure in the hydrogenation reactor is in the range of about 200 psia to 600 psia (about 1,379 kPa to about 4,137 kPa).

10. The method of claim 3 wherein the reactor of step (a) comprises a plurality of adiabatic packed bed reaction zones with inter-stage cooling.

11. The method of any one of claims 1 and 2 wherein the high boiler column distillate comprises about 99.5 wt % CL.

12. The method of any one of claims 1 and 2 further comprising introducing the high boiler column tails to a wiped film evaporator and recovering CL from the high boiler column tails.

* * * * *